United States Patent
Wang et al.

(10) Patent No.: US 10,483,329 B2
(45) Date of Patent: Nov. 19, 2019

(54) HOLE TRANSPORTING MATERIAL, HOLE TRANSPORTING LAYER, OLED DISPLAY PANEL ELECTRONIC DEVICE COMPRISING THE SAME

(71) Applicants: SHANGHAI TIANMA AM-OLED CO., LTD., Shanghai (CN); TIANMA MICRO-ELECTRONICS CO., LTD., Shenzhen (CN)

(72) Inventors: Xiangcheng Wang, Shanghai (CN); Wei He, Shanghai (CN); Ying Liu, Shanghai (CN); Jinghua Niu, Shanghai (CN); Yuji Hamada, Shanghai (CN)

(73) Assignees: SHANGHAI TIANMA AM-OLED CO., LTD., Shanghai (CN); TIANMA MICRO-ELECTRONICS CO., LTD., Shenzhen (CN)

( * ) Notice: Subject to any disclaimer, the term of this patent is extended or adjusted under 35 U.S.C. 154(b) by 190 days.

(21) Appl. No.: 15/666,923

(22) Filed: Aug. 2, 2017

(65) Prior Publication Data
US 2017/0330918 A1 Nov. 16, 2017

(30) Foreign Application Priority Data
Dec. 28, 2016 (CN) .......................... 2016 1 1235778

(51) Int. Cl.
*H01L 27/32* (2006.01)
*H01L 51/00* (2006.01)
(Continued)

(52) U.S. Cl.
CPC ........ *H01L 27/3211* (2013.01); *C07C 211/61* (2013.01); *H01L 51/006* (2013.01);
(Continued)

(58) Field of Classification Search
CPC . C07C 211/54; C07C 211/61; H01L 27/3211; H01L 51/0059; H01L 51/006
See application file for complete search history.

(56) References Cited

U.S. PATENT DOCUMENTS

| 6,517,957 | B1 * | 2/2003 | Senoo | C07C 211/61 313/504 |
| 2003/0207153 | A1 * | 11/2003 | Senoo | C07C 211/61 428/690 |

(Continued)

FOREIGN PATENT DOCUMENTS

| CN | 1571763 A | 1/2005 |
| CN | 105359289 A | 2/2016 |

(Continued)

OTHER PUBLICATIONS

"Organic and Printed Electronics: Fundamentals and Applications" edited by Nisato et al., published by CRC Press Taylor & Francis Group on Mar. 24, 2016, Chapter 6 by Mydlak and Volz.*

(Continued)

*Primary Examiner* — Vu A Nguyen
(74) *Attorney, Agent, or Firm* — Alston & Bird LLP (57) ABSTRACT

The present disclosure relates to a hole transporting material having a structure of formula (I). The present disclosure provides a hole transporting material having at least one fluorenyl ring and having one non-hydrogen substituent on at least one benzene ring in the formula and being capable of obtaining a suitable mobility rate without occurrence of crosstalk between pixels. And the hole transporting material provided by the present disclosure is capable of satisfying the requirements on mask cleaning with solubility (in NMP solvent).

18 Claims, 2 Drawing Sheets

(51) Int. Cl.
    *C07C 211/61*     (2006.01)
    *H01L 51/50*     (2006.01)

(52) U.S. Cl.
    CPC ...... *H01L 51/0052* (2013.01); *H01L 51/0058* (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

2006/0017376 A1* 1/2006 Okinaka ............ H01L 51/5012 313/504
2016/0104843 A1* 4/2016 Kobayashi ............ H01L 51/006 136/254

FOREIGN PATENT DOCUMENTS

| | | |
|---|---|---|
| CN | 106057863 A | 10/2016 |
| EP | 0 879 868 A2 | 11/1998 |
| EP | 0879868 A2 | 11/1998 |
| EP | 0 953 624 A1 | 11/1999 |
| EP | 0953624 A1 | 11/1999 |
| WO | 9509147 A1 | 4/1995 |
| WO | 2017002644 A1 | 1/2017 |

OTHER PUBLICATIONS

SciFinder Search Results (Partial), Apr. 3, 2019.*
Okumoto et al., Chemistry Letters 2000 (pp. 1034-1035), published by the Chemical Society of Japan.*
German Office Action with English Translation, dated Feb. 12, 2019.

* cited by examiner

HOLE TRANSPORTING MATERIAL, HOLE TRANSPORTING LAYER, OLED DISPLAY PANEL ELECTRONIC DEVICE COMPRISING THE SAME

CROSS-REFERENCE TO RELATED APPLICATIONS

The application claims the benefit of the earlier filing date of C.N. Patent Application No. CN201611235778.6, filed on Dec. 28, 2016, the contents of which are incorporated by reference herein in its entirety.

TECHNICAL FIELD

The present application relates to the field of organic light-emitting diodes, and more particularly to material used for hole transporting, a hole transporting layer, and OLED display panel and electronic devices comprising the same.

BACKGROUND

Figure 1:
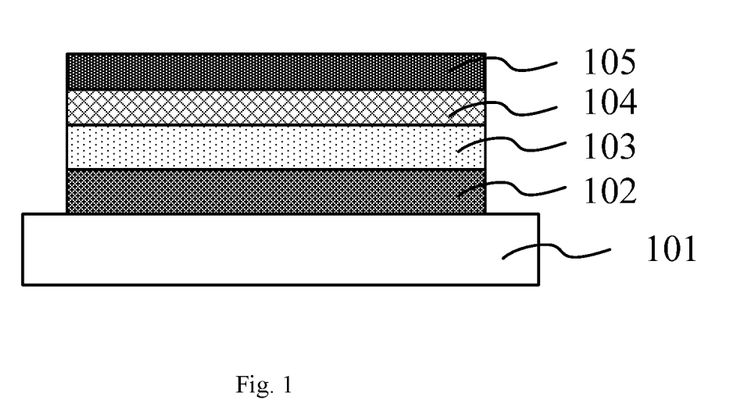
FIG. 1 shows a partial schematic cross-sectional structure view of an OLED display panel according to one specific embodiment of the present disclosure.

Mobile phones and many other small and medium sized OLED screens use R, B sub-pixel display mode (FIG. 1). In order to improve the production yield, some functional layers are often designed as shared layers, reducing fine metal mask (FMM) usage. Hole transporting layer often uses a shared layer, and shared hole transporting layer may consist commercially available materials. The commercially available hole transporting layer materials may include a molecular structure as, (e.g. EP-721935). However, such materials show higher longitudinal mobility rate, but the lateral mobility rates are not very high. There will be no occurrence of crosstalk between pixel. Patent CN103108859 discloses a material structure wherein the material has a good solubility, and a higher mobility rate than the EP-721935 type. There are several problems in the current technologies of hole transporting materials. First, the material solubility is not good, which will lead to a worse cleaning effect of Mask for evaporation during mass production. Second, the material mobility rate is too low, which will lead to an excessive overall voltage of devices. Third, the mobility rate of the material, especially the lateral mobility rate of the material, is too high, leading to crosstalk of adjacent pixels.

The mobility rate of the commercially available material in EP-721935 falls within the acceptable range, and no crosstalk will occur. However, the solubility thereof is not very good. The solubility of the commercially available material in CN103108859 is acceptable, but too high mobility rate leads to lateral leakage current to form crosstalk. Accordingly, there is a need to develop a hole transporting material having a suitable mobility rate without the occurrence of crosstalk between adjacent pixels.

BRIEF SUMMARY OF THE DISCLOSURE

In view of the deficiencies of the related arts, one object of the present disclosure is to provide a hole transporting material having a structure of formula (I):

Formula (I)

wherein $L_1$ is anyone selected from the group consisting of substituted or unsubstituted fluorenylidene, and substituted or unsubstituted biphenylene; the two benzene rings in substituted or unsubstituted fluorenylidene are connected with the two nitrogen atoms in formula (I); the two benzene rings in substituted or unsubstituted biphenylene are connected with the two nitrogen atoms in formula (I);

$L_2$, $L_3$, $L_4$ and $L_5$ each is independently selected from the group consisting of substituted or unsubstituted fluorenyl, and substituted or unsubstituted dibiphenyl; $L_2$, $L_3$, $L_4$ and $L_5$ are connected with nitrogen atoms via a benzene ring;

$L_2$, $L_3$, $L_4$ and $L_5$ in the structure of formula (I) meet at least one of the following conditions:
(1) $L_1$ is substituted or unsubstituted fluorenylidene,
(2) at least one of $L_2$, $L_3$, $L_4$ and $L_5$ is substituted or unsubstituted fluorenyl;
at least one hydrogen atom on at least one benzene ring in the structure of formula (I) is substituted by a non-hydrogen group.

The second object of the present disclosure is to provide a hole transporting layer comprising the hole transporting material as stated in the first object of the present disclosure.

The third object of the present disclosure is to provide an OLED display panel comprising a first electrode and a second electrode, wherein a laminate comprising a light emitting layer and a hole transporting layer is provided between the first electrode and the second electrode; the hole transporting layer comprises the hole transporting material as stated in the first object, or the hole transporting layer is the hole transporting layer as stated in the second object of the present disclosure. The fourth object of the present disclosure is to provide an electronic device comprising the OLED display panel as stated in the third object. As compared to the existing techniques, the present disclosure has the following beneficial effects:
(1) The present disclosure provides a hole transporting material having at least one fluorenyl ring and one non-hydrogen substituent on at least one benzene ring in the formula, and being capable of obtaining a suitable mobility rate without occurrence of crosstalk between pixels. (2) The hole transporting material provided by the present disclosure is capable of satisfying the requirements on mask cleaning in areas of solubility (like N-methylpyrrolidone e.g. NMP solvent). The mask cleaning solvent is selected from the group consisting of ketones, furans or alcohols, or a combination of at least two selected therefrom. Cyclohexanone (HC), (NMP), substituted or unsubstituted furan, isopropyl alcohol and the like are more commonly used.

DETAILED DESCRIPTION

For the purpose of understanding the present disclosure, the present disclosure discloses the following examples. Those skilled in the art shall know that the examples are merely illustrative of the present disclosure and should not be construed as limiting the present disclosure.

In one specific embodiment, the present disclosure provides a hole transporting material having a structure of formula (I), Formula (I)

wherein $L_1$ is anyone selected from the group consisting of substituted or unsubstituted fluorenylidene, and substituted or unsubstituted biphenylene; the two benzene rings in substituted or unsubstituted fluorenylidene are connected with the two nitrogen atoms in formula (I); the two benzene rings in substituted or unsubstituted biphenylene are connected with the two nitrogen atoms in formula (I);

$L_2$, $L_3$, $L_4$ and $L_5$ are each independently anyone selected from the group consisting of substituted or unsubstituted fluorenyl, and substituted or unsubstituted dibiphenyl; $L_2$, $L_3$, $L_4$ and $L_5$ are connected with nitrogen atom via benzene ring;

$L_2$, $L_3$, $L_4$ and $L_5$ in the structure of formula (I) meet at least one of the following conditions (1) $L_1$ is substituted or unsubstituted fluorenylidene,

(2) at least one of $L_2$, $L_3$, $L_4$ and $L_5$ is substituted or unsubstituted fluorenyl;

at least one hydrogen atom on at least one benzene ring in the structure of formula (I) is substituted by non-hydrogen group.

The exemplary substituted or unsubstituted fluorenylidene is selected from the group consisting of alkyl-substituted fluorenylidene, alkenyl-substituted fluorenylidene, aryl-substituted fluorenylidene, and amino-substituted fluorenylidene, optionally C1-C6 alkyl-substituted fluorenylidene, C2-C6 alkenyl-substituted fluorenylidene, C5-C8 aryl-substituted fluorenylidene, amino-substituted fluorenylidene, wherein the typical but non-limitative examples comprise -continued and the like.

The exemplary substituted or unsubstituted biphenylene is selected from the groups consisting of alkyl-substituted biphenylene, alkenyl-substituted biphenylene, aryl-substituted biphenylene, and amino-substituted biphenylene, optionally C1-C6 alkyl-substituted biphenylene, C2-C6 alkenyl-substituted biphenylene, C5-C8 aryl-substituted biphenylene, amino-substituted biphenylene, wherein the typical but non-limitative examples comprise

-continued and the like.

The exemplary substituted or unsubstituted fluorenyl is selected from the groups consisting of alkyl-substituted fluorenyl, alkenyl-substituted fluorenyl, aryl-substituted fluorenyl, and amino-substituted fluorenyl, optionally C1-C6 alkyl-substituted fluorenyl, C2-C6 alkenyl-substituted fluorenyl, C5-C8 aryl-substituted fluorenyl, amino-substituted fluorenyl, wherein the typical but non-limitative examples comprise and the like.

The exemplary substituted or unsubstituted dibiphenyl is selected from the group consisting of alkyl-substituted dibiphenyl, alkenyl-substituted dibiphenyl, aryl-substituted dibiphenyl, and amino-substituted dibiphenyl, optionally C1-C6 alkyl-substituted dibiphenyl, C2-C6 alkenyl-substituted dibiphenyl, C5-C8 aryl-substituted dibiphenyl, amino-substituted dibiphenyl, wherein the typical but non-limitative examples comprise -continued and the like.

In one specific embodiment, $L_1$ in formula (I) is anyone selected from the groups consisting of or a combination of at least two selected therefrom,
wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are each independently anyone selected from the group consisting of hydrogen atom, deuterium atom, linear chain or branched chain alkyl group of C1-C5, and linear chain or branched chain alkoxy group of C1-C5;
$L_2$, $L_3$, $L_4$ and $L_5$ in formula (I) are anyone selected from the group consisting of or a combination of at least two selected therefrom;
wherein $R'_1$, $R'_2$, $R'_3$, $R'_5$, $R'_6$, $R'_7$, $R'_8$, $R'_9$, $R'_{10}$, $R'_{11}$, $R'_{12}$, $R'_{13}$, $R'_{14}$, $R'_{15}$, $R'_{16}$, $R'_{17}$, and $R'_{18}$ are each independently anyone selected from the group consisting of hydrogen atom, deuterium atom, linear chain or branched chain alkyl group of C1-C5, and linear chain or branched chain alkoxy group of C1-C5.

Examples of the linear chain or branched chain alkyl groups of C1-C5 include methyl, ethyl, n-propyl, n-butyl, t-butyl, pentyl and the like.

Examples of the linear chain or branched chain alkoxy groups of C1-C5 include methoxy, ethoxy, n-propoxy, t-butoxy and the like.

In one specific embodiment, $L_1$ in formula (I) is anyone selected from the group consisting of

In one specific embodiment, $L_2$, $L_3$, $L_4$ and $L_5$ in formula (I) are each independently anyone selected from the group consisting of and there is necessarily one fluorenyl ring in formula (I).

As one preferred specific embodiment, $L_3$ and $L_5$ are the same; and $L_2$ and $L_4$ are the same.

As one preferred specific embodiment, the hole transporting material is anyone selected from the group consisting of -continued

, and or a combination of at least two selected therefrom.

In one specific embodiment, the hole transporting material has a hole mobility rate of $9\times10^{-5}$-$5\times10^{-4}$ cm$^2$/V·S, and a solubility in NMP of 10 g/L or more at 25° C.

The mobility rate of $9\times10'$-$5\times10^{-4}$ cm$^2$/V·S can ensure no occurrence of crosstalk between pixels, and the solubility of 10 g/L or more in NMP can meet the mask cleaning requirements.

In one specific embodiment, the present disclosure further provides a hole transporting layer comprising the hole transporting material as stated above.

Optionally, the hole transporting layer has a thickness of 600-2300 Å, e.g. 620 Å, 660 Å, 690 Å, 730 Å, 750 Å, 780 Å, 800 Å, 830 Å, 850 Å, 870 Å, 900 Å, 930 Å, 950 Å, 970 Å, 990 Å, 1020 Å, 1060 Å, 1090 Å, 1130 Å, 1150 Å, 1180 Å, 1200 Å, 1230 Å, 1250 Å, 1270 Å, 1300 Å, 1330 Å, 1350 Å, 1370 Å, 1390 Å, 1400 Å, 1430 Å, 1450 Å, 1470 Å, 1490 Å, 1500 Å, 1530 Å, 1650 Å, 1670 Å, 1790 Å, 1800 Å, 1930 Å, 1950 Å, 2070 Å, 2190 Å, 2200 Å, 2330 Å, 2450 Å, 2470 Å, 2490 Å and the like.

Optionally, the hole transporting layer is doped with a P-type organic material in the hole transporting material as stated above.

Optionally, the p-type organic material has a doping ratio of 1 to 10 wt % in the hole transporting layer, e.g. 2 wt %, 3 wt %, 4 wt %, 5 wt %, 6 wt %, 7 wt %, 8 wt %, 9 wt % and the like.

The present disclosure further provides an OLED display panel comprising a first electrode and a second electrode, wherein a laminate comprising a light emitting layer and a hole transporting layer is provided between the first electrode and the second electrode; the hole transporting layer comprises the hole transporting material above, or the hole transporting layer is the hole transporting layer above.

The exemplary material of the first electrode is anyone selected from the group consisting of indium tin oxide, indium zinc oxide and tin dioxide, or a combination of at least two selected therefrom.

The exemplary material of the second electrode is anyone selected from the group consisting of magnesium, aluminum, silver, or a combination of at least two selected therefrom.

In one preferred specific embodiment, the laminate further comprises anyone of a hole injection layer, a hole transporting layer, an electron transporting layer, and an electron injection layer, or a combination of at least two selected therefrom.

The exemplary material of the hole injection layer is anyone selected from the groups consisting of TDATA (  ),

2-TNATA and TCTA or a combination of at least two selected therefrom.

The exemplary material of the electron transporting layer is anyone selected from the group consisting of BPhen tri-(8-hydroxyquinoline) and TPBi or a combination of at least two selected therefrom.

In one specific embodiment, the light emitting layer comprises anyone selected from the group consisting of a blue light emitting unit, a green light emitting unit and a red light emitting unit, or a combination of at least two selected therefrom.

Optionally, the blue light emitting unit, the green light emitting unit and the red light emitting unit have a common hole transporting layer comprising the hole transporting materials above, or the common hole transporting layer is the hole transporting layer above.

Optionally, the common hole transporting layer has a thickness of 600-2300 Å, e.g. 620 Å, 660 Å, 690 Å, 730 Å, 750 Å, 780 Å, 800 Å, 830 Å, 850 Å, 870 Å, 900 Å, 930 Å, 950 Å, 970 Å, 990 Å, 1020 Å, 1060 Å, 1090 Å, 1130 Å, 1150 Å, 1180 Å, 1200 Å, 1230 Å, 1250 Å, 1270 Å, 1300 Å, 1330 Å, 1350 Å, 1370 Å, 1390 Å, 1400 Å, 1430 Å, 1450 Å, 1470 Å, 1490 Å, 1500 Å, 1530 Å, 1650 Å, 1670 Å, 1790 Å, 1800 Å, 1930 Å, 1950 Å, 2070 Å, 2190 Å, 2200 Å, 2330 Å, 2450 Å, 2470 Å, 2490 Å and the like.

In one specific embodiment, the green light emitting unit and the red light emitting unit adopt a phosphorescent material; and the blue light emitting unit uses a fluorescent material.

In one specific embodiment, the OLED display panel has a red light external quantum efficiency of 16% or more, a green light external quantum efficiency of 16% or more, and a blue light external quantum efficiency of 10% or more.

In one specific embodiment, the laminate further comprises anyone selected from the group consisting of a hole injection layer, an electron transporting layer, and an electron injection layer, or a combination of at least two selected therefrom.

In one specific embodiment, the OLED display panel comprises in turn from bottom to top a first electrode, a hole injection layer, a hole transporting layer, a light emitting layer, an electron transporting layer, an electron injection layer, and a second electrode.

In one specific embodiment, the first electrode is an anode, and the second electrode is a cathode.

In one specific embodiment, the OLED display panel of the present disclosure illustratively has the structure shown in FIG. 1, including a substrate 101, a first electrode 102 disposed on the substrate 101, a hole transporting layer 103 and a light emitting layer 104 sequentially stacked on the first electrode 102, and a second electrode 105 formed thereon.

Figure 2:
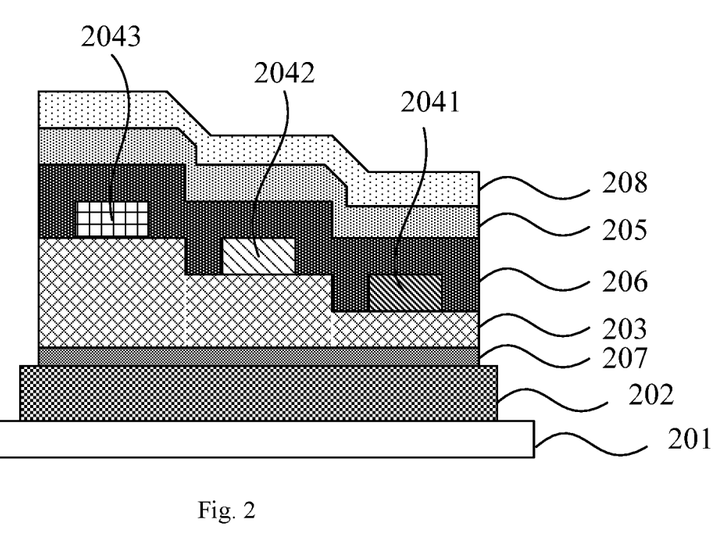
FIG. 2 shows a partial schematic cross-sectional structure view of another OLED display panel according to one specific embodiment of the present disclosure.

In another specific embodiment, the OLED display panel of the present disclosure illustratively has the structure of FIG. 2, including a substrate 201, a first electrode 202 disposed on the substrate 201, a buffer layer 207, a hole transporting layer 203 and an electron transporting layer 206 sequentially stacked on the first electrode 202, and a second electrode 205 formed thereon, and a cap layer 208 overlying the second electrode 205. On the hole transporting layer 203, there are also a blue light emitting unit 2041, a green light emitting unit 2042, and a red light emitting unit 2043, wherein the electron transporting layer 206 covers the blue light emitting unit 2041, the green light emitting unit 2042, and the red light emitting unit 2043, as well as the gaps between the blue light emitting unit 2041, the green light emitting unit 2042, and the red light emitting unit 2043.

The hole transporting layer 203 may be a layer having a uniform thickness or a layer having different thicknesses for different light emitting units. For example, the hole transporting layer is thicker between the red light emitting unit 2043 and the buffer layer 207. Next is the thickness of the hole transporting layer between the green light emitting unit 2042 and the buffer layer 207. The thickness of the hole transporting layer between the blue light emitting unit 2041 and the buffer layer 207 is minimum.

Figure 3:
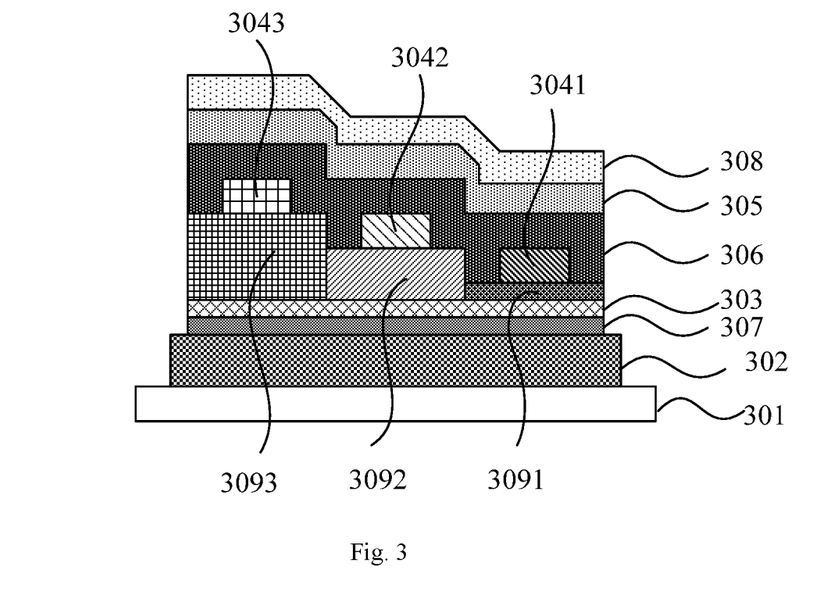
FIG. 3 shows a partial schematic cross-sectional structure view of yet another OLED display panel according to another specific embodiment of the present disclosure.

In yet another specific embodiment, the OLED display panel of the present disclosure illustratively has the structure of FIG. 3, including a substrate 301, a first electrode 302 disposed on the substrate 301, a buffer layer 307, a common hole transporting layer 303, an independent hole transporting layer (red light independent hole transporting layer 3093, green light independent hole transporting layer 3092, and blue light independent hole transporting layer 3091) and an electron transporting layer 306 sequentially stacked on the first electrode 302, and a second electrode 305 formed thereon, and a cap layer 308 overlying the second electrode 305. A red light emitting unit 3043 is provided on the red light independent hole transporting layer 3093 of the independent hole transporting layer; a green light emitting unit 3042 is provided on the green light independent hole transporting layer 3092 of the independent hole transporting layer; a blue light emitting unit 3041 is provided on the blue light independent hole transporting layer 3091 of the independent hole transporting layer. The electron transporting layer 306 covers the blue light emitting unit 3041, the green light emitting unit 3042, and the red light emitting unit 3043 and the gaps between the blue light emitting unit 3041, the green light emitting unit 3042, and the red light emitting unit 3043.

Those skilled in the art shall know that the OLED display panels listed in the present disclosure are not capable of exemplifying all of the structures, and those skilled in the art can also design the display panel according to actual situations. For example, those skilled in the art can set up different thicknesses to the hole transporting layers corresponding to the red light emitting unit, the blue light emitting unit and the green light emitting unit, so as to satisfy the microcavity effect produced by the light emitting units of different colors. Those skilled in the art can also provide an exclusive transporting layer between the light emitting unit and the common hole transporting layer. For example, a red light-hole transporting unit is provided between the luminescent material of the red light emitting unit and the common hole transporting layer; a green light-hole transporting unit is provided between the luminescent material of the green light emitting unit and the common hole transporting layer; and a blue light-hole transporting unit is provided between the luminescent material of the blue light emitting unit and the common hole transporting layer.

Figure 4:
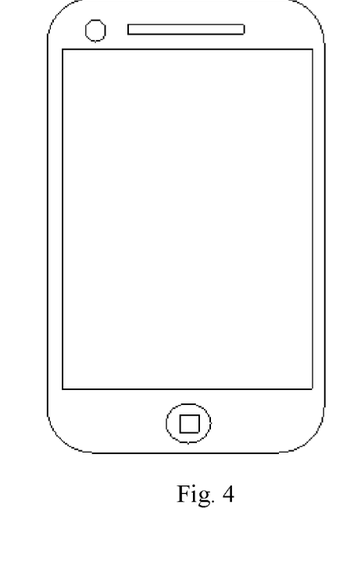
FIG. 4 shows a schematic structure view of an electronic device comprising the OLED display panel according to one specific embodiment of the present disclosure.

The present disclosure further provides an electronic device comprising the OLED display panel above. FIG. 4 illustrates an exemplary electronic device consistent with disclosed embodiments. The device may comprise any of the disclosed OLED display panels. Other components may also be included. The device may be a smart wearable device, a tablet, a TV, a smartphone, a notebook, and a digital frame, etc. Further, the device may be any appropriate type of content-presentation devices. Because the electronic device may comprise any of the disclosed OLED display panels, the device may also exhibit the same advantages as the disclosed OLED display panels, which are not repeated here.

The compounds of the present disclosure having a structure represented by formula (I) can be synthesized by the prior art, for example:

when $L_3$ and $L_5$ are the same, and $L_2$ and $L_4$ are the same, the preparation process can be simplified as:

Synthesis Example 1

-continued 5 g (13.8 mmol) of an intermediate 1, 2.3 g (6.9 mmol) of an intermediate 2, 30.9 mg (0.138 mmol) of palladium acetate and 1.1 g (13.9 mmol) of sodium t-butoxide were added to a 500 mL three-necked flask. The flask was filled with nitrogen; 100 mL of dehydrated toluene and 0.12 mL (0.276 mmol) of tri-tert-butylphosphine were added to the flask. The mixture was placed in an oil bath and slowly heated to 110° C. for 8 hours and allowed to stand overnight. The resulted solid was dissolved in dichloromethane, and washed with 300 mL of saturated brine, and the organic layer was dried with magnesium sulfate. Recrystallization was made by using a mixed solvent of toluene and ethanol to give 4.3 g (5.0 mmol) of a target compound with a yield of 72%. Mass spectrometry M/Z=900.6 was obtained by LC-MS.

Synthesis Example 2

5 g (14.3 mmol) of an intermediate 3, 2.4 g (6.9 mmol) of an intermediate 4, 30.9 mg (0.138 mmol) of palladium acetate and 1.1 g (13.9 mmol) of sodium t-butoxide were added to a 500 mL three-necked flask. The flask was filled with nitrogen; 100 mL of dehydrated toluene and 0.12 mL (0.276 mmol) of tri-tert-butylphosphine were added to the flask. The mixture was placed in an oil bath and slowly heated to 110° C. for 8 hours and allowed to stand overnight. The resulted solid was dissolved in dichloromethane, washed with 300 mL of saturated brine, and the organic layer was dried with magnesium sulfate. Recrystallization was made by using a mixed solvent of toluene and ethanol to give 4.4 g (4.9 mmol) of a target compound with a yield of 71%. Mass spectrometry M/Z=888.9 was obtained by LC-MS.

Example 1

An OLED display panel having the structure shown in FIG. 2 was prepared by the following process.

On the substrate 201 of glass material, a reflective silver anode of 100 nm was formed, and then an ITO film layer was deposited at a film thickness of 15 nm to obtain a first electrode 202 as an anode. Then a mixed material of was evaporated as a buffer layer, wherein the mixing ratio was 5:95 (by weight).

Thereafter, was vacuum-evaporated by using a fine metal mask to form films having thicknesses of 210 nm, 170 nm and 130 nm respectively on red light, green light and blue light pixels, so as to give a hole transporting layer 203 having a hole mobility rate of $3.5 \times 10^{-4}$ cm$^2$/V·S and a solubility in NMP of 22 g/L. 40 nm of and was evaporated at a ratio of 95:5 to form an emission red light emitting unit 2043; 40 nm of and was evaporated at a ratio of 9:1 to form an emission green light emitting unit 2042; 30 nm of and was evaporated at a ratio of 95:5 to form an emission blue light emitting unit 2041; an evaporation material of and was co-evaporated at a ratio of 1:1 to form an electron transporting layer 206 having a thickness of 30 nm, and then to form a magnesium-silver (having a mass ratio of silver to magnesium of 9:1) alloy having a thickness of 15 nm as the second electron 205. 60 nm of a cap layer 208 8-hydroxy-quinoline aluminum was evaporated, and then covered with protective glass sheets.

Example 2

It is different from Example 1 that the material of the hole transporting layer was replaced with wherein the hole mobility rate was $3\times10^{-4}$ cm²/V·S; and the solubility thereof in NMP was 28 g/L.

Example 3

It is different from Example 1 that the material of the hole transporting layer was replaced with wherein the hole mobility rate was $5\times10^{-4}$ cm²/V·S; and the solubility thereof in NMP was 30 g/L.

Example 4

It is different from Example 1 that the material of the hole transporting layer was replaced with wherein the hole mobility rate was $4\times10^{-4}$ cm²/V·S; and the solubility thereof in NMP was 35 g/L.

Comparison Example 1

It is different from Example 1 that the material of the hole transporting layer was replaced with wherein the hole mobility rate was $3\times10^{-4}$ cm²/V·S; and the solubility thereof in NMP was 1.2 g/L.

Comparison Example 2

It is different from Example 1 that the material of the hole transporting layer was replaced with wherein the hole mobility rate was $3.2\times10^{-4}$ cm²/V·S; and the solubility thereof in NMP was 5.2 g/L.

Comparison Example 3

It is different from Example 1 that the material of the hole transporting layer was replaced with wherein the hole mobility rate was $3.5\times10^{-4}$ cm$^2$/V·S; and the solubility thereof in NMP was 2.9 g/L.

Comparison Example 4

It is different from Example 1 that the material of the hole transporting layer was replaced with

, wherein the hole mobility rate was $2\times10^{-4}$ cm$^2$/V·S; and the solubility thereof in NMP was 2.2 g/L.

Performance Tests

Performance tests of the OLED display panels in the Examples and Comparison Examples were carried out.

(1) Device voltage test method: the program being transferred to the B screen, testing the voltage of the blue light at 10 mA/cm$^2$;

(2) Crosstalk test method: the program being transferred to the B screen in a dark room, testing the intensity ratio of the green light of adjacent pixels when the blue light intensity was 0.1 Cd/m$^2$, $L_{Green}/LB_{lue}$;

(3) Mask Cleaning Effect:
the time required for all the materials on the MASK of the red light of the hole transporting layer 203 to be completely cleaned at a fixed ultrasonic frequency of 40 kHz and at a temperature of 25° C.

Test results can be seen in Table 1.

TABLE 1

|  | Device voltage | $L_{Green}/L_{Blue}$ | Mask cleaning time |
|---|---|---|---|
| Example 1 | 98% | 1.9% | 35 |
| Example 2 | 101% | 1.5% | 25 |
| Example 3 | 96% | 3.1% | 25 |
| Example 4 | 98% | 2.7% | 25 |
| Com. Example 1 | 100% | 1.5% | 80 s |

TABLE 1-continued

|  | Device voltage | $L_{Green}/L_{Blue}$ | Mask cleaning time |
|---|---|---|---|
| Com. Example 2 | 100% | 1.8% | 60 s |
| Com. Example 3 | 100% | 1.5% | 55 s |
| Com. Example 4 | 103% | 1.7% | 65 s |

The present disclosure illustrates the detailed process equipment and process flow by the above-described examples, but the present disclosure is not limited to the above-described detailed process equipment and process flow. That is to say, it does not mean that the present disclosure cannot be carried out unless the above-described detailed process equipment and process flow are used. Those skilled in the art shall know that any improvements to the present disclosure, equivalent replacements of the raw materials of the present disclosure, addition of auxiliary ingredients, selection of specific means and the like all fall within the protection and disclosure scope of the present disclosure.

What is claimed is:

1. A hole transporting material, having a structure of formula (I),

Formula (I)

wherein $L_1$ is selected from the group consisting of substituted or unsubstituted fluorenylene, and substituted or unsubstituted biphenylene; wherein the two benzene rings in substituted or unsubstituted fluorenylene, are connected with the two nitrogen atoms in formula (I); wherein the two benzene rings in substituted or unsubstituted biphenylene, are connected with the two nitrogen atoms in formula (I);

$L_2$, $L_3$, $L_4$ and $L_5$ each is independently selected from the group consisting of substituted or unsubstituted fluorenyl, and substituted or unsubstituted biphenylyl; wherein $L_2$, $L_3$, $L_4$ and $L_5$ are connected with nitrogen atoms via benzene rings;

wherein $L_2$, $L_3$, $L_4$ and $L_5$ in the structure of formula (I) meet:

(1) $L_1$ is substituted or unsubstituted fluorenylene, and/or

(2) at least one of $L_2$, $L_3$, $L_4$ and $L_5$ is substituted or unsubstituted fluorenyl;

wherein in the structure of formula (I), at least one hydrogen atom on at least one benzene ring is substituted by a non-hydrogen group, wherein the fluorenylene or fluorenyl is not deemed as being formed by substitution of at least one hydrogen atom on at least one benzene ring therein; and wherein the hole transporting material has a hole mobility of $9\times10^{-5}$-$5\times10^{-4}$ cm$^2$/Vs, and a solubility of 10 g/L or more in NMP at 25° C.

2. The hole transporting material claimed in claim 1, wherein $L_1$ is selected from the group consisting of or a combination of at least two said groups, wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ each is independently selected from the group consisting of a hydrogen atom, a deuterium atom, linear chain or branched chain of alkyl groups of C1-C5, and linear chain or branched chain alkoxy group of C1-C5;

wherein $L_2$, $L_3$, $L_4$ and $L_5$ in formula (I) each is selected from the group consisting of or a combination of at least two selected;

wherein $R'_1$, $R'_2$, $R'_3$, $R'_4$, $R'_5$, $R'_6$, $R'_7$, $R'_8$, $R'_9$, $R'_{10}$, $R'_{11}$, $R'_{12}$, $R'_{13}$, $R'_{14}$, $R'_{15}$, $R'_{16}$, $R'17$, and $R'_{18}$ each is independently selected from the group consisting of a hydrogen atom, a deuterium atom, a linear chain or a branched chain alkyl group of C1-C5, and linear chain or branched chain alkoxy group of C1-C5.

3. The hole transporting material in claim 1, wherein $L_1$ in formula (I) is selected from the group consisting of

-continued $L_2$, $L_3$, $L_4$ and $L_5$ each independently is selected from the group comprising consisting of wherein at least one fluorenyl ring exists in formula (I).

4. The hole transporting material in claim 1, wherein $L_3$ and $L_5$ are the same; and $L_2$ and $L_4$ are the same.

5. The hole transporting material in claim 1, which is anyone of

6. A hole transport layer comprising the hole transporting material of claim 1, wherein the hole transport layer is doped with a p-type organic material.

7. The hole transporting layer in claim 6, having a thickness of 600-2300 Å.

8. The hole transporting layer in claim 6, wherein the p-type organic material has a doping density of 1 to 10 wt % in the hole transporting layer.

9. An OLED display panel comprising a first electrode and a second electrode, wherein a laminate comprising a light emitting layer and a hole transporting layer is provided between the first electrode and the second electrode, and wherein the hole transporting layer comprises the hole transporting material of claim 1.

10. The OLED display panel in claim 9, wherein the light emitting layer comprises at least one of a blue light emitting unit, a green light emitting unit and a red light emitting unit, or a combination of at least two of said units.

11. The OLED display panel in claim 9, wherein the light emitting layer comprises a blue light emitting unit, a green light emitting unit and a red light emitting unit, and the blue light emitting unit, the green light emitting unit and the red light emitting unit have a common hole transporting layer comprising said hole transporting material.

12. The OLED display panel in claim 11, wherein the common hole transporting layer has a thickness of 600-2300 Å.

13. The OLED display panel in claim 10, wherein the green light emitting unit and the red light emitting unit comprises a phosphorescent material; and wherein the blue light emitting unit comprises a fluorescent material.

14. The OLED display panel in claim 10, wherein a red light external quantum efficiency is 16% or more, a green light external quantum efficiency is 16% or more, and a blue light external quantum efficiency is 10% or more in the OLED display panel.

15. The OLED display panel in claim 11, wherein the laminate further comprises at least one of a hole injection layer, an electron transporting layer, and an electron injection layer, or a combination of at least two selected therefrom.

16. The OLED display panel in claim 11, wherein the OLED display panel comprises a first electrode, a hole injection layer, a hole transporting layer, a light emitting layer, an electron transporting layer, an electron injection layer, and a second electrode sequencially.

17. The OLED display panel in claim 11, wherein the first electrode is an anode, and the second electrode is a cathode.

18. An electronic device comprising the OLED display panel in claim 17.

* * * * *